United States Patent [19]

Lazaro et al.

[11] Patent Number: 5,175,001

[45] Date of Patent: Dec. 29, 1992

[54] VANADYL ORGANO-MINERAL COMPOUND, METHOD FOR OBTAINING SUCH A COMPOUND, PHARMACEUTICAL COMPOSITION CONTAINING THIS ORGANO-MINERAL COMPOUND

[75] Inventors: René Lazaro, Clapiers; Gérard Cros, Montpellier, both of France; John H. McNeill, Delta, Canada; Jean-Jacques Serrano, Montpellier, France

[73] Assignee: Panmedica, S.A., Carros Cedex, France

[21] Appl. No.: 656,945

[22] Filed: Feb. 19, 1991

Related U.S. Application Data

[62] Division of Ser. No. 230,520, Aug. 10, 1988, Pat. No. 5,023,358.

[30] Foreign Application Priority Data

Aug. 11, 1987 [FR] France ............... 87 11425

[51] Int. Cl.$^5$ .............................. A61K 9/48
[52] U.S. Cl. .................... 424/451; 424/464
[58] Field of Search .......................... 424/451

[56] References Cited

U.S. PATENT DOCUMENTS 5,023,358 6/1991 Lazaro et al. .............. 556/42

Primary Examiner—Thurman K. Page
Assistant Examiner—Leon R. Horne
Attorney, Agent, or Firm—Kenyon & Kenyon

[57] ABSTRACT

The present invention concerns a vanadyl organo-mineral compound which is in the form of a complex of vanadyl and of cystein, having the following general formula:

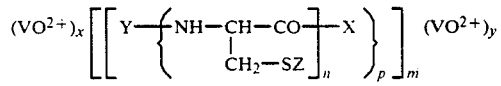

wherein, either x is 1 and y is 0, or x is 0 and y is 1, and wherein n, p and m are respectively integers with a value of 1 or 2.

2 Claims, 2 Drawing Sheets

VANADYL ORGANO-MINERAL COMPOUND, METHOD FOR OBTAINING SUCH A COMPOUND, PHARMACEUTICAL COMPOSITION CONTAINING THIS ORGANO-MINERAL COMPOUND

This is a division of application Ser. No. 07/230,520 filed Aug. 10, 1988, U.S. Pat. No. 5,023,358.

The present invention concerns generally a vanadyl organo-mineral compound. It has essentially as an object a complex comprising vanadyl, methods for obtaining such a complex and a pharmaceutical composition containing the complex.

The invention finds application in particular in the pharmaceutical industry, for the manufacture of anti-diabetic medicines which can be taken orally.

Many compounds are known for their anti-diabetic activity for patients suffering from insulin-depending diabetes. However, the conventional compositions on the basis of these compounds are taken parenterally.

A few compounds have been discovered which are taken orally. For example, compounds on the basis of vanadate which is the oxydized form of vanadium, such as sodium vanadate which, when taken orally, has an anti-diabetic effect, are known. Indeed, in "Clayton, Arun, and Mc Neill, Science, Mar. 22, 1985, vol. 227, pages 1474–1477", Mc Neill et al. have shown that, by adding sodium vanadate to the drink water of diabetic rats, the glycemia of the rats is normalized and the impairing of the cardiac function associated with diabetes is prevented.

However, the sodium vanadate presents a digestive toxicity due to its very weak absorption which is of about 1 to 3%. The vanadate ($V^{5+}$) presents a number of properties, some of which cause this non-digestive toxicity, for example the property of inhibiting the $Na^+/K^+ATP$ ase enzyme in the absorption mechanisms.

Besides, it is known that on the intra-cellular scale, the vanadium reveals its anti-diabetic activity under the vanadyl ($V^{4+}$) form by facilitating or inducing the phosphorylation of the insulin receptor Now, the vanadyl sulfate $VOSO_4$ administered orally to diabetic rats has an anti-diabetic effect but presents an acute toxicity.

The present invention has as an object to provide a new vanadyl organo-mineral compound which does not present the above mentioned drawbacks in the case of the use of the sodium vanadate and of the vanadyl sulfate, and which is both non-toxic and active as an anti-diabetic compound. Such a compound, which remains in the $V^{4+}$ form in the blood, is better absorbed during the digestion and can diffuse in the tissues in an active form.

According to the present invention, this object is attained by a vanadyl organo-mineral compound in the form of a complex of vanadyl and of cystein. This compound has the following general formula:

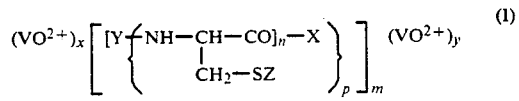

(1)

wherein, either x is 1 and y is 0, or x is 0 and y is 1, and wherein n, p and m are integers respectively equal to 1 or 2.

Such a compound, due to the complexing of the vanadyl ion by a cystein derivative, shows a higher diabetic activity and a lower toxicity than the orally administered anti-diabetic compounds known in the state of the art.

According to a feature of the invention, in the aforesaid formula, x is 1, y is 0, p is 1 and Y is hydrogen and Z is a minus charge. Such a complex has a free amine group.

According to an advantageous feature of the invention, in the aforesaid formula n is 1 and m is 2. The complex is then in the form of a bimolecular ligand.

According to still another advantageous feature of the invention, in the aforesaid formula n is 2 and m is 1. The complex is then in the form of a monomolecular ligand.

According to another feature of the invention, in the aforesaid formula x is 0, y is 1, n is 1, X is a $O^-$ group and Z is hydrogen. This second type of complex has a free carboxyl group.

According to an advantageous feature of the invention, in the aforesaid formula p is 1 and m is 2. The complex is then in the form of a bimolecular ligand.

According to still another advantageous feature of the invention, in the aforesaid formula p is 2 and m is 1. The compound is then a monomolecular ligand.

According to another feature of the invention, in the aforesaid formula x is 0, y is 1, Y is a $CH_2$ group and Z is a minus charge.

According to a characteristic of the invention, in the aforesaid formula n is 1 and p is 1 and m is 2. This compound is a monomolecular ligand with substituted amine and carboxyl groups.

An other object of the invention consists of a method for preparing the vanadyl organo-mineral compound which is in the form of a vanadyl and cystein complex of the formula (I) and which comprises one free amine group or substituted amine and carboxyl groups.

Such a method is characterized:

by reacting a mono- or bifunctional amine or a mono- or bifunctional alcohol, or an amine-alcohol, with the cystein or a derivative thereof, which is protected the amine function and on the thiol function by a tertiobutyloxycarbonyl group in the presence of dicyclohexylcarbodiimide/hydroxybenzotriazole, by eliminating the said tertiobutyloxycarbonyl group by acidolysis, by adding a vanadylsulfate dissolved in water, under a nitrogen atmosphere, to the solution of the hydrochloride of the cystein derivative in a dimethylformamide-borate buffer mixture at a pH of about 10, with a cystein:vanadyl ratio of about 5:1, by recovering the precipitated complex, and by washing with water and drying the said precipitate.

A second method for preparing the compound having one free amine group or substituted amine and carboxyl groups is characterized:

by reacting the cystein or a derivative thereof with vanadyl sulfate at a pH of about 7 in water, by recovering the complex obtained after evaporation, by redissolving the said complex in dimethylformamide, by coupling with a mono- or bifunctional amine, a mono- or bifunctional alcohol or an amine-alcohol, through the medium of dimethylaminopropylethylcarbodiimide, and by recovering the complex after vacuum evaporation of the solvent, and by washing the said complex with ether and with water.

The invention has also as an object a pharmaceutical composition, in particular an anti-diabetic composition, comprising as an active substance the compound such as defined previously.

Such a composition has an anti-diabetic activity and is non-toxic, it can be taken orally, which presents a considerable advantage for the patients suffering from insulin-depending diabetes.

The invention will be better understood and other objects, features and details thereof will appear more clearly as the following explanatory description proceeds, with reference to the illustrative and non limitative examples.

The new vanadyl organo-mineral compound results from the complexing of a vanadyl and of a cystein or cystein derivative and corresponds to the general formula (I).

More precisely, this laevo-rotary (L) or dextro-rotary (D) complex has a free amine group or a free carboxyl group or substituted amine and carboxyl groups.

a) In the case where the ligand comprises a free amine group, it can be bimolecular on the one hand and has the following general formula:

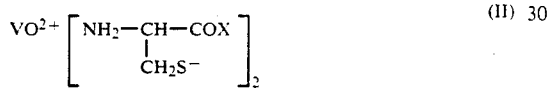

It may be monomolecular, on the other hand, and has therefore the following formula:

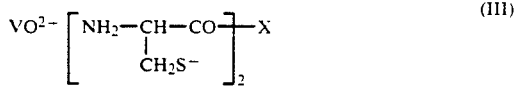

b) In the case where the ligand comprises a free carboxyl group, it can be, similarly, bimolecular on the one hand, and has as a general formula:

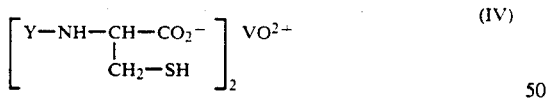

On the other hand, the ligand can be monomolecular and has as a general formula:

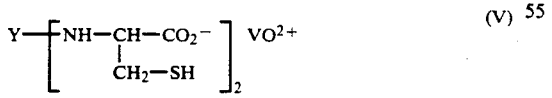

c) in the case where the ligand comprises substituted amine and carboxyl groups, it is in the monomolecular form and has the following general formula:

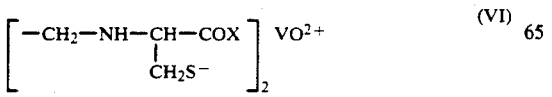

In formulae (II) and (VI), X is a —OR group or a —NHR (amine) group, in which the R moiety is an aryl or aralkyl group or an alkyl group other than methyl.

Therefore, in the case where X is a —NHR group, the organo-mineral compound is for example a complex of vanadyl with an amide of cystein such as in particular a butylamide of cystein or an octylamide of cystein. The vanadyl-octylamide (L) complex of the cystein is illustrated by the following formula:

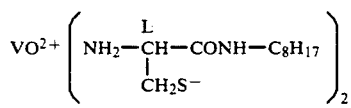

Moreover, in the case where X is a —OR group, the organo-mineral compound is for example a complex of vanadyl with an ester of the cystein such as in particular an octylester of cystein or a butylester of cystein.

Besides, in the formula (III), X corresponds to one of the following groups:

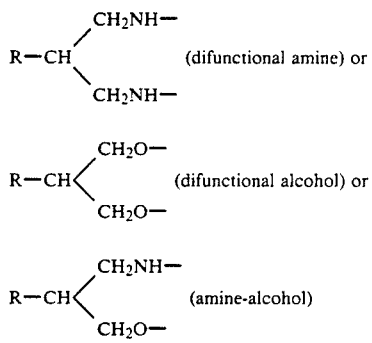

wherein R is an aryl or aralkyl group or an alkyl group other than butyl.

In formula (IV), Y corresponds to a R-CO-(ketone) group in which the R moiety is an alkyl, aryl or aralkyl group.

In formula (V), Y corresponds to one of the following groups:

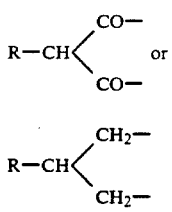

wherein R is also an alkyl, aryl or aralkyl group.

By way of example, the preparation of the compounds, namely the vanadyl complexes of the formulae (II), (III), (IV), (V) and (VI) will be given thereafter.

(i) A method for preparing the compound (II) or (VI) consists in:

reacting a monofunctional amine or a monofunctional alcohol with the cystein or a derivative thereof protected on the amine function and on the thiol function by a BOC or tertiobutyloxycarbonyl group in the presence of dicyclohexylcarbodiimide/hydroxybenzotriazole, eliminating the said BOC or tertiobutyloxycarbonyl group by acidolysis with the aid of hydrochloric acid and dioxan, adding vanadylsulfate which is dissolved in water, under a nitrogen atmosphere, to the solution of the hydrochloride of the cystein derivative in a dimethylformamide-borate buffer mixture at a pH of about 10 with a cystein/vanadyl ratio of 5/1, then, stirring the mixture for 2 hours in a nitrogen atmosphere, recovering the complex formed by precipitation, by means of a filtration, and washing with water and drying the precipitate.

The product obtained presents the following characteristics. It is insoluble in water and in ethylether. On the other hand, it is soluble in DMF or dimethylformamide and in methanol.

The example 1 below illustrates an embodiment of this method in the case of the preparation of a complex of vanadyl and of an octylamide of the cystein.

(ii) The preparation of the compound of formula (III) consists in reacting a bifunctional amine or a bifunctional alcohol or an amine-alcohol with the cystein or a derivative thereof. The remaining procedure is identical to that of the above described method of preparation.

(iii) Another method for preparing the compound of formula (II) or (VI), consists in:

reacting the cystein or derivative thereof with vanadyl sulfate at a pH of about 7 in water, recovering the complex obtained after evaporation, redissolving the complex formed in dimethylformamide as above, coupling with a monofunctional amine or with a monofunctional alcohol through the medium of dimethylaminopropylethylcarbodiimide, and recovering the complex after vacuum evaporation of the solvent, washing with ether and with water, dissolution in methanol, evaporation and reprecipitation by ethylether.

This method is illustrated by example 2 below in the case of the preparation of a complex of vanadyl with cystein octylamide.

(iv) The preparation of the compound (III) proceeds with the same steps as the method mentioned above for the preparation of compounds (II) and (VI), however, as starting product, a bifunctional amine or a bifunctional alcohol or an amine-alcohol is reacted with the cystein or a derivative thereof.

(v) The method of preparing the compound of formula (IV) where Y corresponds to the R-CO-group, consists in:

coupling the activated derivative (ester or chloride) of the R-COOH acid with the cystein previously protected on its thiol function by a BOC group, deprotecting then the thiol function by acidolysis; and complexing the obtained N-acylated derivative with the vanadyl in a DMF-water medium at a pH of 10, such a medium containing the vanadyl sulfate.

(vi) Finally, the method for preparing the compound of formula (V) where Y corresponds to:

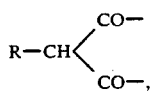

consists in:

coupling the activated derivative (ester or chloride) of the diacid

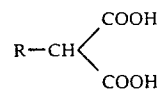

with the cystein previously protected on the thiol function by a BOC group, deprotecting the thiol function by acidolysis, reducing the N-acylated derivative thus obtained; and then complexing this N-acylated derivative in a DMF-water medium at a pH of 10, in the presence of vanadyl sulfate.

EXAMPLE 1

According to the above method (i), vanadyl sulfate dissolved in water is reacted with a solution of the hydrochloride of the cystein octylamide having the following formula:

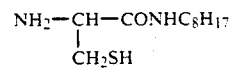

in an atmosphere of nitrogen in a dimethylformamide-borate buffer mixture (pH of about 10) with a cystein to vanadyl molar ratio of 5:1. The product is obtained by precipitation.

By means of a quantitative analysis of vanadium by atomic absorption, there is obtained a stoichiometry of 2:1 of the cystein with respect to vanadyl and a weight percentage of vanadium of about 9.6%+0.2%.

The product thus obtained is a bimolecular complex or ligand.

Figure 1:
FIG. 1 graphically shows by analysis that vanadium is in the vanadyl form.

Moreover, the analysis by electronic paramagnetic resonance with reference to FIG. 1, presents resonance bands with a hyperfine structure. It results from this analysis that vanadium is in the VO$^{2+}$ vanadyl form.

Consequently, the vanadyl organo-mineral compound thus obtained has as a formula:

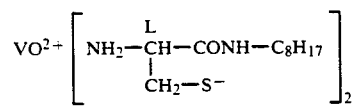

EXAMPLE 2

The vanadyl sulfate is coupled with the cystein octylamine corresponding to the above mentioned method (iii).

The compound obtained is a complex (L) of vanadyl and of the cystein octylamide with the formula:

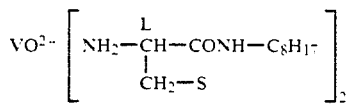

The above defined vanadyl organo-mineral compound is used in particular in the pharmaceutical industry. More particularly, it has been shown that a pharmaceutical composition containing as an active substance such a complex has an anti-diabetic activity and is non-toxic. Thus, such above described vanadyl organo-mineral derivatives are therapeutic substitutes of the insulin, which can be taken orally in the case of insulin-depending diabetes.

First, the potential toxicity of the complex has been investigated.

The investigation has been carried out starting from the bimolecular vanadyl compound having one free amine group, of the general formula (II). After a unique oral administration to the rat, the measured toxicity of the compound of formula (II) on the one hand and of the vanadyl sulfate on the other hand have been compared.

The procedure of the toxicological tests is as follows.

On the one hand, the toxicity of the compound (II) is examined by administering orally increasing doses of compound (II), up to 1 g/kg, to a group of 10 male rats of the WISTAR strain with a mean weight of 150 g. A quantity of 10 ml/kg of a suspension of compound (II) in 3% gum arabic is administered, by forcible feeding, to animals which have not been fed. Then, the animals are examined for 14 days, in order to count for the deaths and to search and observe the signs of toxicity.

On the other hand, the acute toxicity of the vanadyl sulfate ($VOSO_4$) is contemplated under similar conditions on animals divided into 7 groups of 10 animals to which the following doses have been administered: 300, 400, 500, 600, 800, 1000 and 1500 mg/kg.

The lethal dose ($LD_{50}$) has been calculated by the method of LITCHFIELD AND WILCOXON.

The results are as follows.

On rats which have absorbed compound (II), no visible sign of toxicity is observed up to the dose of 1 g/kg. The dose of 1 g/kg corresponds to about 20 times the active anti-diabetic dose.

On rats which have absorbed the vanadyl sulfate, the $LD_{50}$ is set at 600 mg/kg. The first signs of toxicity are already observed at the dose of 400 mg/kg. The toxicity appears in the form of a diarrhoea with a variable seriousness, a decrease of the motor activity and a loss of flesh. For the higher doses: 800, 1000 and 1500 mg/kg, hypothermia and cases of chromodacryorrhoea are observed.

Therefore, the vanadyl organo-mineral compound is not toxic when compared to the vanadyl sulfate, for administration doses of the compound up to 1 g/kg.

Then, the anti-diabetic activity of the above described complex of vanadyl and cystein has been examined.

The examination has been performed also starting from the compound with the formula (II). The activity of this compound has been compared on diabetic rats and on non-diabetic rats, and the activity of this compound (II) has been compared with that of the vanadyl sulfate.

Tests have been carried out on animals having a glycemia higher than 3 g/l.

The method is as follows. Diabetes is induced by intraveinous injection of a unique dose of streptozotocin of about 50 mg/kg, on male or female rats of the WISTAR strain with a mean weight of 200 g. The glycemia is measured 4 days after the injection.

The procedure of the pharmacological tests is as follows. A quantity of 45 mg/kg of compound (II) is administered by forcible feeding (doses of 10 ml/kg) to animals which have been fed, in the form of a suspension in a 3% solution of gum arabic. A dose of vanadyl sulfate equimolar to 45 mg/kg of compound (II) is administered.

The glycemia is measured by quantitative analysis. Blood is sampled from the tail of the animal. The glycemia is measured by means of a device named "AMES glucometer" (trade-mark). The rate of glycemia is read on "Derotrostix" dipsticks (trade-mark) of the aforesaid device.

Besides, the insulinemia is measured with a radio-immunological kit named "AMERSHAM" (trade-mark).

The results are as follows.

Figure 2:
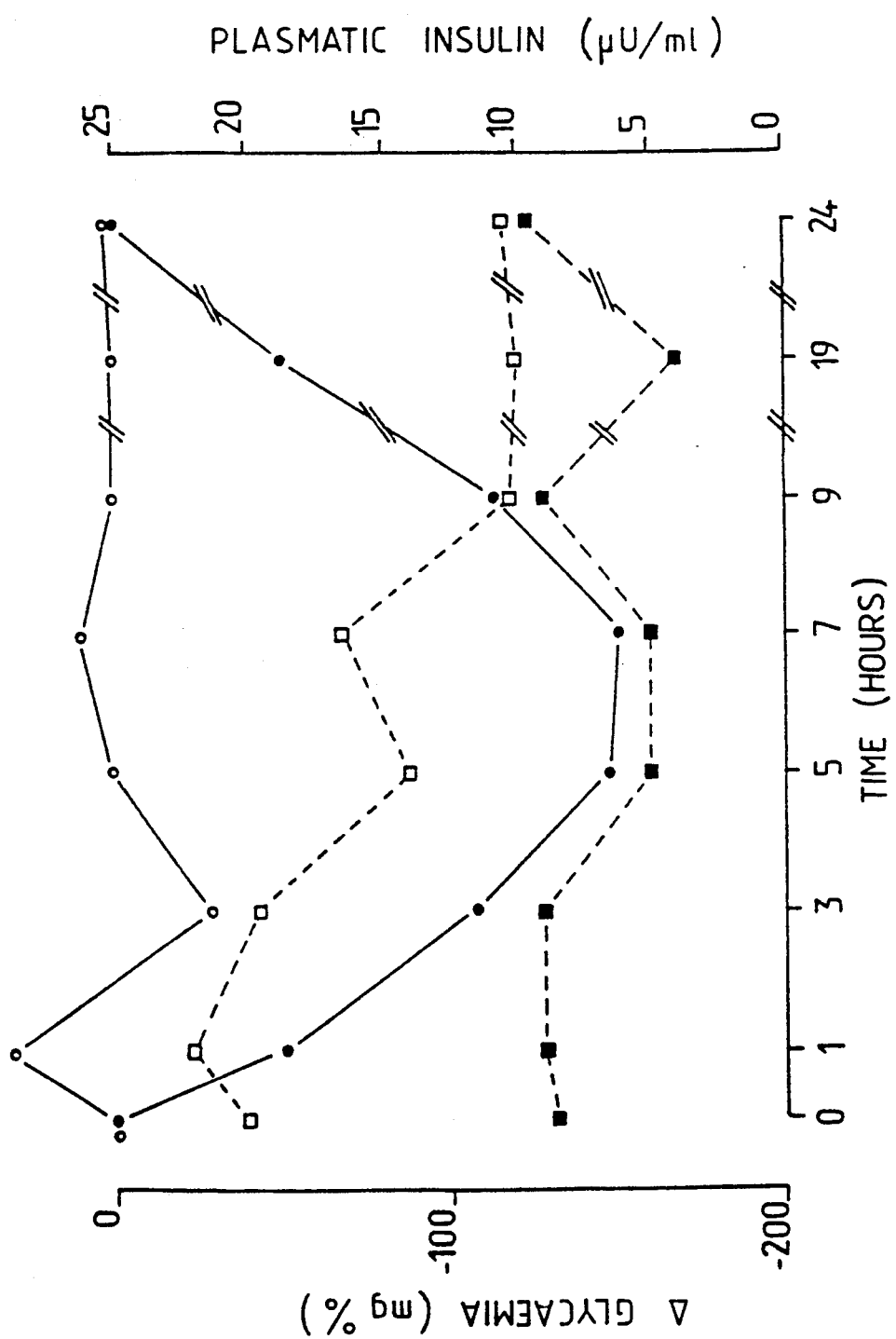
FIG. 2 shows the effect, graphically, of administration of compound (II).

Referring to FIG. 2, there is shown the effect of a unique administration of compound (II) with a dose of 45 mg/kg on the glycemia and on the insulinemia of diabetic or non-diabetic animals.

On FIG. 2, —○— corresponds to the effect of the oral administration of 45 mg/kg of compound (II) on the glycemia of non-diabetic animals; —●— corresponds to the effect of the oral ration of 45 mg/kg of compound (II) on the glycemia of diabetic animals; ---□--- corresponds to the effect of the oral administration of 45 mg/kg of compound (II) on the insulinemia of non-diabetic animals; ---■--- corresponds to the effect of the oral administration of 45 mg/kg of compound (II) on the insulinemia of diabetic animals.

On the diabetic animals, the administration of compound of formula (II) induces a drop of the glycemia for about 24 hours. The maximum effect is located between the fifth and the seventh hour after the administration. After 7 hours, the glycemia decreases progressively and attains a normal rate such as that of non-diabetic animals.

It is to be noted here that the glycemia of non-treated diabetic or non-diabetic animals does not deviate from the base value of more than 0.2 g/l during the experimental period contemplated.

Moreover, it is to be noted also that the administration of a vanadyl sulfate dose equimolar to 45 mg/kg of compound (II) induces a weaker and transitory decrease of the glycemia of diabetic animals. Indeed, the maximal decrease is of about 1 g/l and the duration of the effect is limited to 2 hours after the administration.

Consequently, the vanadyl organo-mineral compound, when administered orally at a non-toxic dose, presents hypoglycemic properties on the diabetic animals only. The action of this compound is prolonged in the time and is higher than that of the vanadyl sulfate.

Concerning the insulinemia, FIG. 2 shows that it decreases or remains stable on diabetic or non-diabetic animals.

Therefore, the administration of compound (II) does not induce the production of insulin. There is no hyperinsulinemia. On the contrary, a drop of insulinemia is observed. Under these conditions, the above described vanadyl organo-mineral compound replaces the insulin which presents a surprising advantage. Indeed, the antidiabetic action of the compound is not coupled with an increase of the insulinemia.

In view of the foregoing, the complexing of the vanadyl ion by a cystein derivative permits obtaining a higher anti-diabetic activity and a lower toxicity with respect to that of vanadyl sulfate, and is not coupled with a hyperinsulinemia.

Thus, pharmaceutical compositions are prepared from the above described complex as the active substance. Besides the vanadyl organo-mineral derivative, these pharmaceutical compositions comprise excipients.

They are either in a solid form such as capsules, pills or the like, or in a soluble form such as a suspension or drops or the like.

The patients suffering from insulin-depending diabetes can then have an oral treatment and therefore avoid any obligation in relation with a parenteral treatment, without any risk of toxicity.

What is claimed is:

1. A pharmaceutical composition in a solid form such as capsules, pills comprising as an active substance a vanadyl organo-mineral compound in the form of a complex of a vanadyl and of cysteine with the following general formula:

$$(VO)\left([Y-\{NH-CH-CO]_n-X\}_p \atop CH_2-SH\right)_m \quad (I)$$

wherein n, p and m are integers equal to 1 or 2 respectively and wherein when p=1 then: Y is selected from the group consisting of a hydrogen atom and a R'-CO group; and (a) when n=1 and m=2, X is selected from the group consisting of an OH group, an OR group and a NHR group wherein R is selected from the group consisting of an alkyl group different from a methyl group comprising from 2 to 9 carbon atoms;

wherein:
when X=an OH group; Y≦a R'-CO group wherein R' is selected from the group consisting of an alkyl group comprising from 2 to 9 carbon atoms, and,
when X is selected from the group consisting of an OR group and an NHR group; Y is H; and (b) when n=2 and m=1, X selected from the group consisting of:

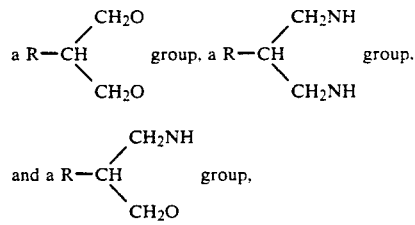

and a R—CH(CH₂NH)(CH₂O) group, wherein R is selected from the group consisting of an alkyl group other than butyl comprising from 2 to 9 carbon atoms; and wherein p=2 then:
n=1, m=1, X=an OH group, Y is selected from the group consisting of

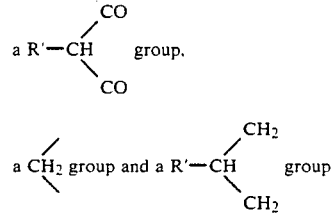

wherein R' is selected from the group consisting of an alkyl group comprising from 2 to 9 carbon atoms.

2. A pharmaceutical composition according to claim 1, useful for obtaining an oral anti-diabetic medicine.

* * * * *

UNITED STATES PATENT AND TRADEMARK OFFICE
CERTIFICATE OF CORRECTION

PATENT NO. : 5,175,001
DATED : December 29, 1992
INVENTOR(S) : Rene Lazaro

It is certified that error appears in the above-indentified patent and that said Letters Patent is hereby corrected as shown below:

Column 2, line 42, After "protected" insert --on--.

Column 6, line 26, Change "$CONHC_8H_{17}$" to --$CONH\ C_8H_{17}$--.

Column 7, line  5, Change "$CH_2-S$" to -- $CH_2-S-$ --.

Column 8, line 32, Change "ration" to --administration--.

Column 1, line  2, Change "$Y \leqq a\ R'-CO$" to --$Y = a\ R'-CO$--.

Signed and Sealed this

First Day of March, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,175,001
DATED : December 29, 1992
INVENTOR(S) : Rene Lazaro

It is certified that error appears in the above-indentified patent and that said Letters Patent is hereby corrected as shown below:

Column 2, line 42, After "protected" insert --on--.

Column 6, line 26, Change "$CONHC_8H_{17}$" to --$CONH\ C_8H_{17}$--.

Column 7, line 5, Change "$CH_2-S$" to -- $CH_2-S^-$ --.

Column 8, line 32, Change "ration" to --administration--.

Column 1, line 2, Change "$Y \leqq a\ R'-CO$" to --$Y = a\ R'-CO$--.

Signed and Sealed this

Tenth Day of May, 1994

Attest:

BRUCE LEHMAN

Attesting Officer    Commissioner of Patents and Trademarks